US009265965B2

(12) United States Patent
Fox et al.

(10) Patent No.: US 9,265,965 B2
(45) Date of Patent: Feb. 23, 2016

(54) APPARATUS AND METHOD FOR DELIVERY OF TRANSCRANIAL MAGNETIC STIMULATION USING BIOLOGICAL FEEDBACK TO A ROBOTIC ARM

(71) Applicants: Peter T. Fox, San Antonio, TX (US); Jack L. Lancaster, San Antonio, TX (US)

(72) Inventors: Peter T. Fox, San Antonio, TX (US); Jack L. Lancaster, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 661 days.

(21) Appl. No.: 13/628,509

(22) Filed: Sep. 27, 2012

(65) Prior Publication Data

US 2013/0085316 A1    Apr. 4, 2013

Related U.S. Application Data

(60) Provisional application No. 61/541,234, filed on Sep. 30, 2011.

(51) Int. Cl.
*A61N 2/00* (2006.01)
*A61N 2/02* (2006.01)

(52) U.S. Cl.
CPC . *A61N 2/02* (2013.01); *A61N 2/006* (2013.01)

(58) Field of Classification Search
CPC ......... A61N 2/00; A61N 2/002; A61N 2/004; A61N 2/006; A61N 2/008; A61N 2/02; A61N 1/36021; A61N 1/36025
See application file for complete search history.

(56) References Cited

U.S. PATENT DOCUMENTS

| 4,864,966 A | 9/1989 | Anderson et al. |
|---|---|---|
| 4,937,759 A | 6/1990 | Vold |
| 4,940,453 A | 7/1990 | Cadwell |
| 4,990,839 A | 2/1991 | Schonlau |
| 5,047,005 A | 9/1991 | Cadwell |
| 5,078,140 A | 1/1992 | Kwoh |
| 5,116,304 A | 5/1992 | Cadwell |
| 5,236,432 A | 8/1993 | Matsen et al. |
| 5,427,097 A | 6/1995 | Depp |
| 5,466,213 A | 11/1995 | Hogan et al. |
| 5,697,285 A | 12/1997 | Nappi et al. |
| 5,725,471 A | 3/1998 | Davey et al. |

(Continued)

FOREIGN PATENT DOCUMENTS

| EP | 0 709 115 | 1/1996 |
|---|---|---|
| GB | 2 261 820 | 6/1993 |

(Continued)

OTHER PUBLICATIONS

Patent Cooperation Treaty, International Search Report Mailed Apr. 7, 2003 in International application No. PCT/US02/14157.

(Continued)

*Primary Examiner* — Charles A Marmor, II
*Assistant Examiner* — Carrie R Dorna
(74) *Attorney, Agent, or Firm* — Trop, Pruner & Hu, P.C.

(57) ABSTRACT

Disclosed are apparatus and methods for computer-aided, robotic delivery of transcranial magnetic stimulation (TMS) using biologically derived feedback to establish coil position relative to brain functional regions. The apparatus includes a TMS coil mounted to a robotic member. The position of the stimulating coil can be automatically optimized using the TMS-induced bio-responses of various types.

15 Claims, 2 Drawing Sheets

(56) References Cited

U.S. PATENT DOCUMENTS

| | | | |
|---|---|---|---|
| 5,806,518 | A | 9/1998 | Mittelstadt |
| 6,013,997 | A | 1/2000 | Heideman et al. |
| 6,035,228 | A | 3/2000 | Yanof et al. |
| 6,048,302 | A | 4/2000 | Markoll |
| 6,076,008 | A | 6/2000 | Bucholz |
| 6,086,525 | A | 7/2000 | Davey et al. |
| 6,099,459 | A | 8/2000 | Jacobson |
| 6,132,361 | A | 10/2000 | Epstein et al. |
| 6,179,770 | B1 | 1/2001 | Mould |
| 6,179,771 | B1 | 1/2001 | Mueller |
| 6,198,958 | B1 | 3/2001 | Ives et al. |
| 6,212,419 | B1 | 4/2001 | Blume et al. |
| 6,266,556 | B1 | 7/2001 | Ives et al. |
| 6,330,467 | B1 | 12/2001 | Creighton et al. |
| 6,366,814 | B1 | 4/2002 | Boveja et al. |
| 6,459,924 | B1 | 10/2002 | Creighton et al. |
| 6,585,746 | B2 | 7/2003 | Gildenberg |
| 6,783,524 | B2 | 8/2004 | Anderson et al. |
| 7,087,008 | B2 | 8/2006 | Fox |
| 2003/0050527 | A1* | 3/2003 | Fox et al. .................. 600/13 |
| 2005/0033380 | A1* | 2/2005 | Tanner et al. .............. 607/45 |
| 2006/0265022 | A1* | 11/2006 | John et al. ................. 607/45 |
| 2010/0298623 | A1* | 11/2010 | Mishelevich et al. ........... 600/13 |

FOREIGN PATENT DOCUMENTS

| WO | WO 98/18384 | 5/1998 |
|---|---|---|
| WO | WO 99/55421 | 11/1999 |

OTHER PUBLICATIONS

Patent Cooperation Treaty, International Preliminary Examination Report Mailed Jul. 8, 2003 in International application No. PCT/US02/14157.

Wasserman, et al., "Locating the Motor Cortex on the MRI with Transcranial Magnetic Stimulation," Feb. 1996, pp. 1-9.

Paus, et al., "Transcranial Magnetic Stimulation During Positron Emission Tomography: A New Method for Studying Connectivity of the Human Cerebral Cortex," May 1, 1997, pp. 3178-3184.

Narayama, et al., "Use of Neurosurgical Robot for Aiming and Holding in Cortical TMS Experiments," Neuroimage, vol. 11, No. 5, 2000, p. S471.

Monique Traad, "A Quantitative Positioning Device for Transcranial Magnetic Stimulation," 1990, p. 2246.

Ilmoniemi, et al., "Transcranial Magnetic Stimulation—A New Tool for Functional Imaging of the Brain," 1999, pp. 241-284.

Krings, et al, "Stereotactic Transcranial Magnetic Stimulation: Correlation with Direct Electrical Cortical Stimulation," Dec. 1997, Neurosurger, vol. 41, No. 6, pp. 1319-1326.

Paus, et al., "Transcranial Magnetic Stimulation During Pet: Reaching and Verifying the Target Site," 1998, Brain Map, Vo. 6, No. 5-6, pp. 399-402.

Paus, "Imaging the Brain Before, During and After Transcranial Magnetic Stimulation," Feb. 1999, pp. 219-224.

Boroojerdi, et al., "Localization of the Motor Hand Area Using Transcranial Magnetic Stimulation and Functional Magnetic Resonance Imaging," Apr. 1999, pp. 699-704.

Davey, "Magnetic Stimulation Coil and Circuit Design," Nov. 2000, pp. 1493-1499.

Hsu, et al., "A 3-D Differential Coil Design for Localized Magnetic Stimulation," Oct. 2001, pp. 1162-1168.

Weh-Hau Lin, et al., "Magnetic Coil Design Considerations for Functional Magnetic Stimulation," May 2000, pp. 600-610.

Ruohonen, et al., "Functional Magnetic Stimulation: Theory and Coil Optimization," 1998, pp. 213-219.

Turner, "A Target Field Approach to Optimal Coil Design," 1986, pp. L147-L151.

Turner, "Minimum Inductance Coils," 1988, pp. 948-952.

Mouchawar, et al., "Guidelines for Energy-Efficient Coils: Coils Designed for Magnetic Stimulation of the Heart," 1991, pp. 255-267.

Cadwell, "Optimizing Magnetic Stimulator Design," 1991, pp. 238-248.

Martens, et al., "Insertable Biplanar Gradient Coils for Magnetic Resonance Imaging," 1991, Am. Inst. of Physics, Vo. 62, No. 11, pp. 2639-2645.

Ruohonen, et al., "Coil Design for REal and Sham Transcranial Magnetic Stimulation," Jan. 2000, IEEE Transactions of Biomedical Engineering, vol. 47, No. 2, pp. 145-148.

Guggisberg, et al., "Motor Evoked Potentials From Masseter Muscle Induced by Transcranial Magnetic Stimulation of the Pyramidal Tract: The Importance of Coil Orientation," Dec. 2001, Clin Neurophysiol. 2001, 112(12), pp. 2312-2319.

Herwig, et al., "The Navigation to Transcranial Magnetic Stimulation," Nov. 30, 2001, Psychiatry Res, 108(2), pp. 123-131.

Brasil-Neto, et al., "Optimal Focus Transcranial Magnetic Activation of the Human Motor Cortex: Effects of Coil Orientation, Shape of the Induced Current Pulse, and Stimulus Intensity," 1992, 6 pages.

Krings, et al., "Representation of Cortical Motor Function as Revealed by Stereotactic Transcranial Magnetic Stimulation," Nov. 14, 1997, 10 pages.

Miranda, et al., "A New Method for Reproducible Coil Positioning in Transcranial Magnetic Stimulation Mapping," Dec. 20, 1996, 8 pages.

European Patent Office, Notice of Opposition dated Apr. 26, 2012 in EP application/patent No. 02724022.5-2319/1383572.

W. Paulus, et al., "Transcranial Magnetic Stimulation," Proceedings of the Intl Symposium on Transcranial Magnetic Stimulation, Sep. 30-Oct. 4, 1998, 12 pages.

* cited by examiner

Figure 1. Biologically Based Aiming Work Flow

FIG. 2

APPARATUS AND METHOD FOR DELIVERY OF TRANSCRANIAL MAGNETIC STIMULATION USING BIOLOGICAL FEEDBACK TO A ROBOTIC ARM

This application claims priority to U.S. Provisional Patent Application No. 61/541,234 filed on Sep. 30, 2011, entitled Apparatus And Method For Delivery Of Transcranial Magnetic Stimulation Using Biological Feedback To A Robotic Arm.

BACKGROUND

The present invention is directed to apparatus and methods particularly suitable for precise aiming and delivery of magnetic stimulation, and more specifically, transcranial magnetic stimulation.

Transcranial magnetic stimulation ("TMS") is a means of repetitively stimulating the human brain through an intact scalp and skull, i.e., non-invasively. TMS is delivered by passing a brief (200 microsecond), strong (10,000 volts, 6,000 amps) electrical current through a coil of wire (a TMS stimulator) placed adjacent to the head. The passage of electrical current induces a strong (2 Tesla) magnetic field which, in turn, induces electrical currents in nearby tissues. In the case of nerve cells, if the induced current is sufficiently intense and properly oriented, it will result in synchronized depolarization of a localized group of neurons (i.e., neuronal "firing"). Initially, magnetic stimulation was used only for peripheral nerves, in which instance it is affecting nerve fibers rather than neuronal cell bodies. More recently, magnetic stimulation has shown to be able to depolarize neurons in the brain. The cellular element of the brain being affected by TMS was assumed, but not proven, to be fibers rather than neuronal cell bodies.

TMS has several present and potential applications, in the domains of basic neuroscience research and of the treatment of brain disorders. Applications for neuroscience research include, for example: imaging brain connectivity; establishing inter-regional and inter-hemispheric conduction times; testing the function of specific brain areas by means of transient functional disruptions, so-called "virtual lesions"; and, studying the modification of synaptic efficacy induced by repetitive stimulation, termed LTP (long-term potentiation) and LTD (long-term depression). Potential clinical applications include, for example: pre-operative mapping, e.g., of language related brain areas; testing for neuronal conduction delays due to dysmyelinating disorders; and, treating brain disorders by selective modification (up or down regulation) of the synaptic efficacy of pathways (i.e., by inducing LTP and LTD).

Many TMS delivery systems are very crude. The TMS effector or stimulator (commonly referred to as a "TMS coil") is a wire-wound coil, typically shaped like a "B." The B-shaped coil is placed against the scalp and held in place by a human operator. For the primary motor cortex and primary visual cortex (small sections of the total brain surface), proper positioning is established by the elicited response: muscle contractions when stimulating the primary motor cortex; illusory lights (phosphenes) when stimulating the primary visual cortex. In both of these areas, the effects are very sensitive to coil position and orientation.

Structural and functional brain images can be used to fully specify TMS targeting by a robotic member, including the calculating and achieving optimal position and orientation of the coil relative to the scalp and brain surfaces. One method includes a method for optimally aligning a magnetic field relative to neuronal orientation, as inferred from the cortical surface orientation. Brain images are acquired prior to the TMS treatment session and used to compute an optimal pose (also termed the "treatment plan") which is then robotically implemented in a second, subsequent TMS session.

DETAILED DESCRIPTION

Figure 1:
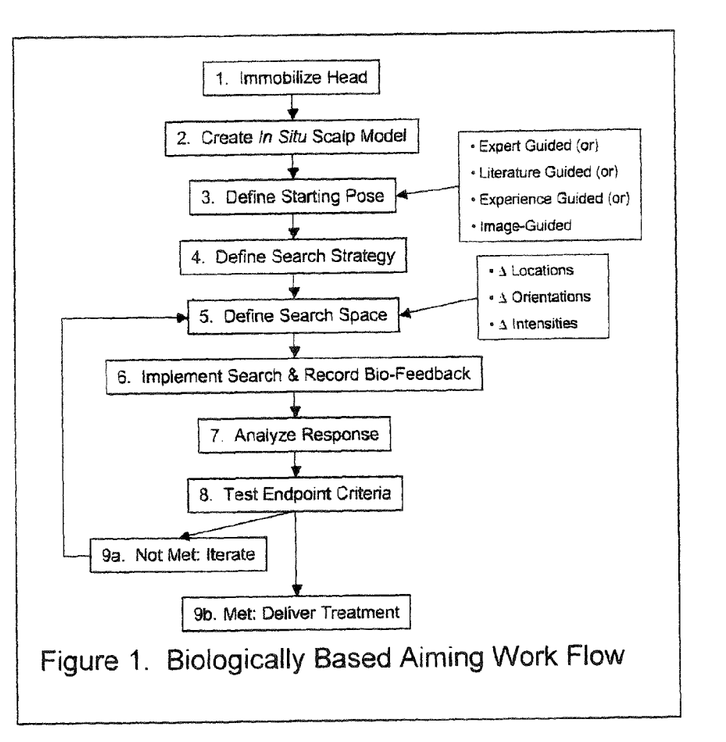
FIG. 1 is a flow diagram of a method in accordance with one embodiment of the present invention.

In various embodiments, a method for using a robotic member to deliver TMS does not rely on prior imaging of the person to be treated. A representative robotic member for use in TMS is described in U.S. Pat. No. 7,087,008, the disclosure of which is hereby incorporated by reference. The steps to perform this delivery, in one embodiment, are shown in FIG. 1: 1) immobilize the head in a manner which allows access to the scalp; 2) create an in situ surface model of the subject's scalp, using a 3-D digitizing system; 3) define a starting (seed) pose of the coil (specifying both location and orientation) on the in situ surface model, using one of a variety of methods, defined below; 4) define a search strategy; 5) define a search domain around the seed location, to include alterations in location, orientation and intensity of TMS stimulation; 6) obtain TMS-induced biological responses, while implementing the defined search; 7) analyze the biological feedback data to characterize response profiles within the search space; 8) use the result of step 6 to test endpoint criteria, for optimal aiming; 9a) if criteria are not met by any pose/intensity within the search space, repeat steps 5-8, iteratively refining the search space; 9b) if endpoint criteria are met by a pose/intensity in the search space, initiate TMS treatment at this site.

A TMS coil is mounted to a multi-jointed robotic member, by which it is both moved into position and held stable during treatment delivery. For example, a TMS coil may be mounted to a NeuroMate neurosurgical robot (IMMI, France). The NeuroMate robotic system was developed specifically for medical uses and is well-suited for TMS delivery. However, a robot not primarily intended for medical use may be modified for this purpose. For example, several robots primarily intended for industrial uses have been adapted for TMS delivery, including: an F3 manufactured by CRS (Burlington, Ontario, Canada), and both the KR16 and the KR5 robots manufactured by KUKA (Augsburg, Bavaria, Germany; Clinton Township, Mich., USA). For all robots, modification includes a coil mounting system and custom movement planning software. For industrial-use robots, software to enhance safety, including speed and workspace limitations are needed. For some robots, additional axes, encoders and extenders are required.

Step 1. Head Immobilization. In the present implementation, it is assumed that the head is immobile throughout the procedure. To achieve immobilization, the head must be restrained. For example, the head can be restrained using an individually molded, thermal plastic facial mask. Alternatively, the head may be immobilized using straps, a bite-bar, an injected-foam, molded head rest, or other suitable system. In come cases, head movement following creation of the scalp model (Step 2) will cause errors. Head motions can be tracked and automatically corrected for by robotic repositioning of the coil relative to the head.

Step 2. In Situ Head-Surface Model. The in situ scalp model is a collection of 3D coordinates describing the head surface. The 3-D coordinates can be collected using a mechanical digitizing arm, such as a Microscribe G2LX (Immersion Corp., San Jose, Calif.) or an optical scanner, such as the FastSCAN laser scanner (Polhemus, Colchester, Vt.), or any other comparable device which registers locations in space and records these location addresses in a format usable by a computer. Combinations of devices can also be used, to optimize digitization of different head surfaces.

The in situ head model may be restricted to the scalp, or include the scalp and face. The scalp is readily accessed, even after head immobilization. Manual digitizers are particularly good for scalp digitization, as the digitizing stylus passes through the hair. Including facial features adds contours to the head-surface model, which can substantially improve fitting speed and goodness of fit. Optical digitizers are well adapted for scanning the face, as hair does not obstruct passage of the laser beam to the skin surface. Once the head surface model is collected, the location of the robotic member and the attached coil must be registered into this same space. This is most readily done by digitizing pre-specified points on the coil (manual digitizer) or scanning the coil surface (optical digitizer), after attachment of the coil to the robotic member. Output from manual and optical scanners may be combined.

Step 3. Define the Starting Pose. Once the head-surface model is created and the location of the robotic member and the attached coil are established relative to the head model, the coil can be moved into contact with the head surface. The initial location of the coil on the head surface is called the starting pose, which is specified in 6-parameters: x, y, and z location address; x, y and z orientation address. The selection of a starting pose can be made by at least three alternative strategies: 1) by a human who has expertise in the functional organization of the human brain; 2) by reference to a standardized space in which functional locations have been reported in the brain-imaging literature; 3) by reference to cumulative experience with TMS, in which effective locations are recorded in standardized space; and, 4) by image-guidance, as disclosed in U.S. Pat. No. 7,087,008. Each of these three strategies is described briefly in the following paragraphs.

Human-Expert-Guided Placement. A person expert in the functional organization of the human brain can designate the starting pose. This can be done in a variety of manners. For example, a hand-held coil can be placed against the head at the desired pose and be digitized while being held in this location. This digitized location can then be used to define the starting pose for the robotically manipulated coil. As a second example, an expert can mark the desired location on the scalp with a pen or other marker. As a third example, the desired location can be identified on the subject's scalp with the tip of a digitizing stylus. As a fourth example, the desired location can be identified by computer model of the in situ scalp, using surface viewing software. For expert placement orientation can be selected or be set to a commonly used default orientation, such as the "B-nose" orientation. In the B-nose orientation, the coil is placed tangential to the scalp with the point of maximum TMS-induced field at the specified target point, but with the forward edge of the coil at a 45-degree angle relative to the midsagittal plane.

Imaging-Literature-Guided Placement. Tens of thousands of peer-reviewed articles report functional brain locations in standardized coordinates. The two most common spaces used for this purpose are that defined by Talairach and Tounoux (1988) and that defined by the MNI standard brain (reference.) Studies reporting in this format typically published their results as x, y, z coordinates in results tables, which can readily obtained directly from the published articles. An alternative standardized space used primarily for electroencephalographic (EEG) and event-related potential (ERP) is defined by the 10-20 electrode system.

Databases collating the results of functional brain imaging studies are accessible on line. For example, over fifty thousand functional brain locations identified by more than six thousand functional brain imaging experiments reported from more than one-thousand, five-hundred peer-reviewed manuscripts have been compiled in the BrainMap database (www.brainmap.org). The BrainMap database reports coordinates in the Talairach space, the MNI space, and other, less popular spaces. The BrainMap site also provides tools for translating coordinates between these alternative spaces, for example, using the Lancaster (et al. 2008) transform. As another example, the CARET database (brainmap.wustl.edu/caret/) provides a smaller sample of data.

Quantitative meta-analysis is a highly effective means of computing population average locations from functional locations reported as standardized coordinates. Tools for quantitative meta-analysis are provided at the BrainMap website (www.brainmap.org). Population average locations are excellent sources for seed locations.

To use seed locations defined from standardized coordinates, the in situ head-surface model (created in step 2) can be referenced to the standardized space(s) in which the literature is reported. This can be done by registering the in-situ head-surface model to the skin surface model of a "standard head". The standard head-surface model is extracted from an image or images which have high quality anatomical information, allowing both the skin surface and internal brain structures to be identified. For example, a T1-weighted magnetic resonance image (MRI) depicts sufficient anatomical detail within the brain to permit registration to the standard anatomical space defined by the anterior and posterior commissures and also allows the skin surface to be automatically delineated. The standard brain image can be that of a single, representative subject or a composite formed from multiple subjects. In either instance, the standard brain will be registered to the standard anatomical space. A common algorithm for registering two head surfaces is "hat and head" algorithm. After registration, the 9-parameter transform and its inverse can be used to transform between coordinates in the in situ head and of the standard space. Alternatively, the convex hull standard model can be used.

Note that the functional imaging literature does provide location address but does not provide orientations. Thus, imaging-literature-guided placement must use a default orientation in the starting pose. The most commonly used default orientation is the "B-nose" orientation (above).

Cumulative-Experience-Guided Placement. In the course of using a TMS delivery system which is capable of recording the spatial address of treatment locations, a body of knowledge is developed regarding the population of effective treatment poses. This knowledge can be obtained and recorded using a robotic system. It can also be obtained using a passive digitizing arm, such as the BrainSight System (Rogue Research, Montreal, Canada). If hand held treatment is supplemented by a system for digitizing the scalp and the treatment location, it can also be obtained with hand-held treatment studies. This cumulative experience can be readily recorded and collated in a laboratory database, for use in specify starting poses, or an on-line databased for effective TMS positions and orientations.

Per-Subject-Image-Guided Placement. In U.S. Pat. No. 7,087,008, structural and functional brain images previously obtained in the subject being studied can be used to define a treatment site. This treatment site can also be considered a starting pose that is refined through the iterative, biological-feedback-based method described herein.

Step 4. Define Overall Search Strategy. The search strategy describes the overall plan for searching, which includes: selection of the modality of biologically derived feedback; defining whether the search will be single-stage or multiple-stage; defining how the search space (or search spaces for an iterative search) will be defined for each stage; defining which analysis algorithms will be employed at each stage; and determining endpoint criteria for each stage. A multiple-stage search might consist of differing search algorithms at different stages. For example, a first-stage search might comprehensively sample a large search space (e.g., 5 cm×5 cm) at large increments (e.g., 1 cm step size) with the entire search space sampled prior to analysis and apply a center-of-mass algorithm to detect local maxima. On the other hand, a late stage search might sample a restricted search space (e.g., 1 cm×1 cm) at fine increments (e.g., 1 mm step size) with analysis performed after each increment, using a gradient descent algorithm. These examples are not intended to be in any way restrictive to the type of search strategies.

Step 5. Define Search Space. The search space is the array of locations, orientations and intensities (i.e., a list of 7-paramater location:orientation:intensity addresses) to be stimulated while obtaining biological feedback (Step 6) prior to response analysis (Step 7). In standardized brain space, the inter-subject location variability of brain functional regions has an average standard deviation (sd) of ~5 mm in each axis. If the TMS coil is positioned at the population average seed location, a search space of plus and minus three sd (3 cm diameter) will include the targeted region in >99% of the population.

Sample spacing within the search space is a function of stimulation intensity. Higher intensities effectively stimulate a larger brain region, allowing sampled locations to be more widely spaced. Lower stimulation intensities effectively stimulate a smaller brain region, necessitating that sampled locations be more closely spaced.

The search space chosen will also be impacted by the search algorithm to be applied (Step 6) and the number of iterations of the search which have already been completed. For example, if a center-of-mass (COM) algorithm is to be applied, the initial search would sample a large extent of widely space location/orientations at a high stimulation intensity. Subsequent iterations of a COM algorithm would search a smaller space, sampled more finely, using a lower stimulation intensity. As a second example, a successive line-minimization (or -maximization) algorithm can be used. If a line-minimization algorithm is used, the initial search space will be smaller. For these algorithms a line direction is initially determined from signal gradient components at a seed point. This line direction indicates the direction of increasing signal. A search is performed along the line to find the line's maximum value. At the line's maximum a new line direction is calculated. The process of calculating line direction and searching for the line's maximum is repeated until the signal maximum is found.

6. Implement Search and Record TMS-Induced Biological Feedback. The search is implemented by delivering TMS stimulation to each specified location:orientation:intensity address while digitally recording a form of biologically derived feedback appropriate to the functional brain region being sought. These forms of biologically derived feedback fall into several broad categories, including: 1) TMS-induced movements; 2) TMS-induced movement alterations, which includes movement delays, errors and other alterations; 3) TMS-induced perceptions; 4) TMS-induced perceptual alterations, which includes perceptual delays, errors and other alterations; 5) TMS-induced cognitive alterations, which includes cognitive delays, errors and other alterations; 6) TMS-induced autonomic effects; and, 7) TMS-induced electrophysiological effects. Each of these will be discussed in turn.

1. TMS-Induced Movements. When primary motor cortex (M1) and some pre-motor regions are stimulated, muscular contractions can be elicited de novo, that is, without requiring an ongoing motor behavior. Muscular contraction, in turn, can cause movement of the skin, digits, limbs, face, eyes and other body parts. The most common examples of TMS-induced de novo movements are finger movements caused by contractions of the intrinsic hand muscles induced by stimulation of the primary motor cortex representations of the hand ($M1_{hand}$). TMS-induced contractions of the first dorsal interosseous muscle (FDI), for example, causes the index finger to move; contractions of the abductor digiti minimi (ADI) muscles cases the fifth digit to move. Examples of movements induced by TMS-stimulation of a non-primary motor region are proximal muscle movements elicited by stimulation of the supplementary motor area (SMA).

TMS-induced movements can be detected by a wide variety of biosensors, including accelerometers, force transducers, optical digitizers, microphones (e.g., for induced vocalization), and so forth. In the present context, any biosensor recording TMS-induced movements for the purpose of automated localization of a functional brain region can be used.

2. TMS-Induced Movement Alterations. When movements are imminent (i.e., a reflexive or mental event is about to trigger initiation of a neural motor program), incipient (i.e., expression of the neural motor program has been triggered), or ongoing, TMS stimulation of involved functional brain regions can alter the intended movement in a variety of ways. Movements can be delayed, accelerated, altered in force, targeted erroneously, be fractionated (i.e. not smooth), have aberrant trajectories, or be altered in other ways. TMS-induced movement alterations can be caused by stimulation of a wide range of areas, including primary motor cortex and pre-primary motor areas. For example, pre-movement stimulation of primary motor cortex (M1), supplementary motor cortex (SMA) and multiple premotor cortex regions will delay movement onset, readily detected by a delayed reaction time to a movement cue. As another example, TMS stimulation of inferior premotor cortex (Brodmann area 6) alters ongoing speech production in a manner similar speech apraxia. As a third example, TMS of the frontal eye fields (FEF; Brodmann area 8) will alter the trajectory of ongoing eye movements.

TMS-induced movement alterations can be detected by a wide variety of biosensors, including accelerometers, force transducers, optical digitizers, microphones (e.g., for vocalization), and so forth. In the present context, any biosensor recording TMS-induced movement alterations for the purpose of automated localization of a functional brain region can be used.

When TMS is used to alter movements, the time of delivery of the TMS pulse(s) relative to the onset of the movement may affect the presence and magnitude of the movement alteration. In this scenario, TMS-stimulus latency relative to movement-cue latency can be varied and used as an additional search-space parameter.

3. TMS-Induced Perceptions. When primary and higher-order sensory cortices are stimulated with TMS, perceptions can be elicited de novo, that is, without requiring an ongoing sensory stimulation or perception. For example, stimulating the primary visual cortex (V1) can cause subjects to perceive a flash of light in a restricted portion of the visual field. As another example, stimulating primary somatosensory cortex can cause subjects to perceive a touch sensation to a restricted portion of the skin surface. As a third example, stimulating primary auditory cortex can cause subjects to perceive illusory sounds. As a fourth example, stimulating the extra-primary visual sensory region alternately termed V5 or MT can cause subjects to perceive illusory motion.

TMS-induced illusory perceptions can be detected by having subjects make a computer-detectable report (e.g., press a response key) for each perception. Further, they can be mapped by having subjects point to or touch the location or direction of the illusory perception. Illusory perceptions can be detected when the subject is unstimulated (e.g., visual percepts in the dark or while the eyes are closed) or interspersed with true stimulations, to more properly calibrate the illusory stimulations. For example, true visual stimulations can be presented at various known positions in the visual field so that the subjects accuracy in indicating direction can be assessed for interpreting responses to illusory percepts.

4. TMS-Induced Perceptual Alterations. When primary and higher-order sensory cortices are stimulated with TMS, perceptions can be altered. Alterations can include failure to perceive a stimulus, distorted or altered perceptions or delayed perceptions. For example, stimulation of primary visual cortex during intermittent presentation of visual stimuli can cause the true stimulus to be unperceived or misperceived and therefore not reported or erroneously reported. Similarly, stimulation of primary somatosensory cortex can cause ongoing tactile stimulations to be unperceived or misperceived. As a third example, stimulating primary auditory cortex can cause subjects to perceive illusory sounds. As a fourth example, stimulating the extra-primary visual sensory region alternately termed V5 or MT can cause subjects to fail to perceive or misperceive motion.

TMS-induced altered perceptions can be detected by having subjects make a computer-detectable report (e.g., press a response key) for each perception detection or discrimination. Failure to respond to a stimulus presented in conjunction with TMS, which is detected in the absence of TMS indicates failure to perceive. Similarly, incorrect responses to a stimulus presented in conjunction with TMS, indicates misperception.

When TMS is used to alter perceptions, the time of delivery of the TMS pulse(s) relative to the onset of the sensory stimulus may affect the presence and magnitude of the perceptual alteration. In this scenario, TMS-stimulus latency relative to sensory-stimulus latency can be varied and used as an additional search-space parameter.

5. TMS-Induced Cognitive Alterations. When higher-order, multi-modal brain regions are stimulated with TMS, cognitive processes carried out by these areas can be interrupted, delayed or altered. Alterations can include failure to perceive a stimulus, distorted or altered perceptions or delayed perceptions. For example, TMS-induced altered perceptions can be detected by having subjects make a computer-detectable report (e.g., press a response key) for each perception detection or discrimination. Failure to respond to a stimulus presented in conjunction with TMS, which is detected in the absence of TMS indicates failure to perceive. Similarly, incorrect responses to a stimulus presented in conjunction with TMS, indicates misperception.

When TMS is used to alter cognition, the time of delivery of the TMS pulse(s) relative to the onset of the sensory stimulus cueing or informing the cognitive task may affect the presence and magnitude of the cognitive alteration. In this scenario, TMS-stimulus latency relative to sensory-stimulus latency can be varied and used as an additional search-space parameter.

6. TMS-Induced Autonomic Effects. Reliable TMS-induced autonomic effects have not yet been reported in the literature. However, it is likely that stimulation of regions associated with emotional responses, such as the insula and its connections, will be able to modulate heart rate, blood pressure, sudomotor responses (sweating), piloerection, gastric motility, and other autonomically modulated physiological processes. Such responses have been reported with direct cortical stimulation during neurosurgical operations (reference). Thus, as TMS technology improves, autonomic effects may become a target.

TMS-induced automonic alterations can be detected by a wide variety of biosensors, as these processes are commonly measured for medical purposes. In the present context, any biosensor recording TMS-induced autonomic alterations for the purpose of automated localization of a functional brain region can be used.

7. TMS-Induced Electrophysiological Effects. TMS stimulation of any brain region is effective by virtue of its alteration of neuronal activity, both at the stimulated site and remotely, through neuronal connection pathways. Altered neuronal activity can be detected electrophysiologicallly by a variety of methods, including electromyography (EMG), electroencephalography (EEG), magnetoencephalography (MEG) and by electrodes inserted directly into the brain. EMG effects are the most widely reported electrophysiologically effect of TMS. EMG effects are the result of direct and indirect (i.e., via inter-neurons) of corticospinal neurons which project via the anterior horn cells of the spinal cord to the body musculature. TMS stimulation of primary motor cortex (M1) causes contractions of contra-lateral muscles, which can be recorded by electrodes placed on the surface of the muscles or inserted into the muscles. This effect is often referred to as the Motor Evoked Potential (MEP). Another electrophysiological effect of M1 stimulation is cessation of the normal levels of neuronal firing for a variable period of time following the MEP wave; this effect is the Cortical Silent Period (CSP). As a third example, stimulation of M1 causes inhibition of the contralateral M1, via inter-hemispheric projections through the corpus callosum, which can be detected by EMG cessation in the muscles ipsi-lateral to the stimulation. As a fourth example of an electrophysiological effect, EEG can be used to record the immediate neural effects of TMS both at the stimulated site and remotely.

Although TMS has not yet been used to target brain regions by virtue of an electrophysiological effect on implanted electrodes. However, implanted electrodes are commonly used for recording from deep structures (e.g., medial temporal lobe) in patients with epilepsy. While TMS cannot yet directly stimulate the medial temporal lobe, it could be used to modulate this region by means of its connections to other brain regions which are amenable to TMS stimulation. Thus, TMS targeting to achieve effects in brain regions with implanted electrodes is both feasible and of potential therapeutic benefit.

TMS-induced electrophysiological effects can be detected by a variety of sensors, including EMG, EEG, MEG and electrodes inserted in the brain. In the present context, any biosensor recording TMS-induced electrophysiological alterations for the purpose of automated localization of a functional brain region can be used.

7. Analyze Response. The analysis performed will be dependent on the type of biological feedback being obtained, the brain region being stimulated, and the search algorithm being applied. For example, if primary motor cortex (M1) is being stimulated and EMG is being recorded from a muscle contra-lateral to the stimulated brain site, EMG data may be analyzed for the distribution of MEG magnitudes within the search space, or the distribution of CSP's within the search space, or both. The response distribution for the search space can be analyzed for the center(s)-of-mass, or for gradients, or for both or for other parameters. If the biologically derived feedback is a reaction time (RT), the analysis would seek the increases (or decreases) in RT. If binary responses are obtained (e.g., detection of a percept, either illusory or real), the detection rate over multiple stimulations will be obtained. Once the analysis is complete, the results are compared to end-point criteria (Step 8).

8. Test Endpoint Criteria. Endpoint criteria define the successful conclusion of the search or a specific stage of searching, when a multiple-stage search is being performed. The specific criteria employed will depend on the definition of the search and the analysis applied. For example, in first-stage center-of-match search, finding a local maxima in which response magnitude is above background by a pre-specified amount may be an adequate endpoint for this stage, which allows the search to move to the next stage, returning to Step 5. In a late-stage search, the search space may specify intensity modulation to include range at which the maxima response point yields a detectable response in <50% of trials, this being a common definition of the M1 motor threshold at the site of maximum response in M1.

9a. Final Criteria Not Met: Iterate. If endpoint criteria are met for a stage, the search moves to the next stage in the strategy prior to iteration. If the endpoint criteria are not met, the search may need to be repeated without modification.

9b. Final Criteria Met: Deliver TMS Treatment. Once the search is concluded and the site for stimulation is defined, the treatment is delivered. In this context, the term "treatment" includes stimulation for the purpose of research or for clinical care (i.e., disease remediation). The treatment site selected is also stored for future use. Future use can be future treatment sessions for the individual subject. Future use can also be to store the treatment location in a database, to facilitate starting pose computation in other, subsequent subjects.

Embodiments thus describe a method for using a robotic member to deliver TMS which does not rely on prior images. This is done by: 1) approximating the region to be stimulated using standard coordinates (i.e., location seeding); and, 2) iteratively refining this location using biologically derived feedback. Thus, this new method is substantially different from prior work (such as the Cortical Column Cosine aiming theory) and methodologically, by using location seeding and biological feedback in lieu of imaging. Embodiments can be implemented, in part, by instructions to be executed by a computer system and stored on a non-transitory storage medium.

Figure 2:
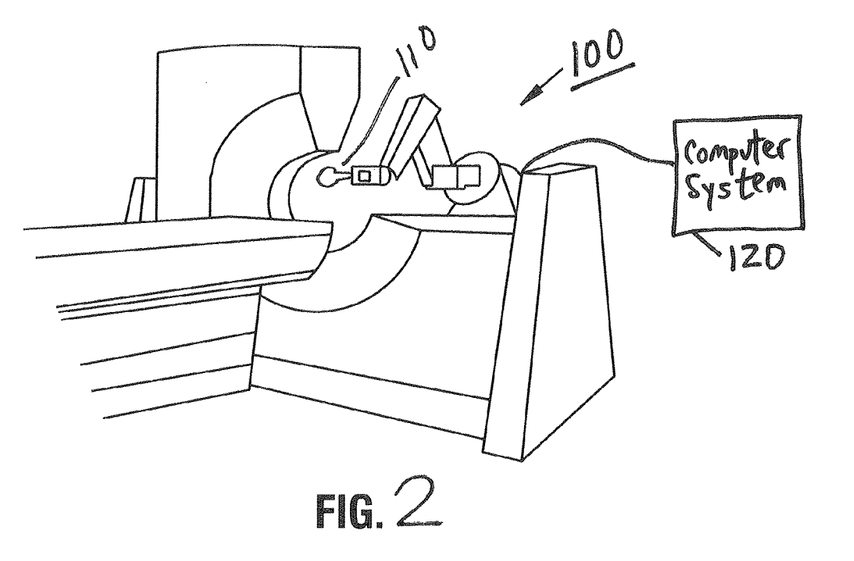
FIG. 2 is a block diagram of a system in accordance with one embodiment of the present invention.

To this end, one or more computers each with a processor and one or more storages may include instructions to perform the described methods for TMS preparation, delivery, analysis, and finally delivery to a localized treatment site for treatment. FIG. 2 is a block diagram of a system in accordance with one embodiment of the present invention. As shown in FIG. 2, a robot 100 having a TMS coil 110 attached to a distal end may be controlled as described herein using a computer 120 that executes one or more sets of instructions stored in a storage of the computer to realize the TMS operations described herein.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method comprising:
    immobilizing a head of a subject in preparation for transcranial magnetic stimulation (TMS) delivered by a TMS stimulator adapted to a robotic member having at least 6 degrees of freedom;
    creating an in situ scalp model of the head using a digitization system;
    defining a starting pose of the TMS stimulator;
    defining a search strategy, including selecting a modality of TMS-induced biological feedback, defining a number of stages of a search space, defining an analysis algorithm for each stage, and defining endpoint criteria for each stage, the search space comprising an array of locations, orientations and intensities to be stimulated;
    defining the search space around the starting pose to be stimulated by the TMS delivery while obtaining the TMS-induced biological feedback during TMS delivery based at least in part on the analysis algorithm;
    delivering the TMS via the TMS stimulator and obtaining the TMS-induced biological feedback during the TMS delivery;
    analyzing the TMS-induced biological feedback;
    testing endpoint criteria for optimal aiming of the TMS delivery, the endpoint criteria to define a successful conclusion of a stage of the number of stages of the search space; and
    delivering the TMS for treatment of the subject when the endpoint criteria are met.

2. The method of claim 1, wherein the starting pose is obtained via at least one of expert guidance, literature guidance, experience guidance or image-guidance.

3. The method of claim 1, wherein the search space is determined by at least one of a location, orientation or intensity.

4. The method of claim 1, further comprising when the endpoint criteria are not met, moving to a next stage of the number of stages of the search space with a refined search space.

5. The method of claim 1, wherein the TMS-induced biological feedback includes one or more of TMS-induced, movement TMS-induced alteration, TMS-induced perception, and TMS-induced physiological effect.

6. The method of claim 5, further comprising obtaining the TMS-induced movement via at least one of an accelerometer, a force transducer, an optical digitizer, and a microphone.

7. The method of claim 1, further comprising delivering the TMS to stimulate a brain region having an implanted electrode.

8. The method of claim 1, wherein analyzing the TMS-induced biological feedback including analyzing for a distribution of magnitudes of the TMS-induced biological feedback within the search space.

9. The method of claim 8, further comprising analyzing the distribution of magnitudes for a center of mass.

10. The method of claim 8, further comprising analyzing the distribution of magnitudes for a gradient.

11. The method of claim 1, further comprising delivering the TMS at a treatment site according to a defined stimulation site, and storing the defined stimulation site in a storage for a future treatment session for the subject.

12. The method of claim 1, further comprising delivering the TMS without using image information of the subject.

13. An article comprising a non-transitory storage medium including instructions that when executed cause a computer system to:

receive an in situ scalp model of a head of a subject undergoing transcranial magnetic stimulation (TMS) delivered by a TMS stimulator adapted to a robotic member having at least 6 degrees of freedom;

define a starting pose of the TMS stimulator;

define a search strategy, including selection of a modality of TMS-induced biological feedback, definition of a number of stages of a search space, definition of an analysis algorithm for each stage, and definition of endpoint criteria for each stage, the search space comprising an array of locations, orientations and intensities to be stimulated;

define the search space around the starting pose to be stimulated by the TMS delivery while obtaining the TMS-induced biological feedback during the TMS delivery based at least in part on the analysis algorithm;

enable delivery of the TMS via the TMS stimulator and obtain the TMS-induced biological feedback during the TMS delivery;

analyze the TMS-induced biological feedback;

test endpoint criteria for optimal aiming of the TMS delivery, the endpoint criteria to define a successful conclusion of a stage of the number of stages of the search space; and enable delivery of the TMS for treatment of the subject when the endpoint criteria are met.

14. The article of claim 13, further comprising instructions to deliver the TMS at a treatment site according to a defined stimulation site, and store the defined stimulation site in a storage for a future treatment session for the subject.

15. A system for transcranial magnetic stimulation, comprising:

a robotic member having a distal portion and a proximal portion, said robotic member having at least six degrees of freedom;

a coil for generating an electric field, said coil coupled to said distal portion of said robotic member;

a computer to receive an in situ scalp model of a head of a subject undergoing transcranial magnetic stimulation (TMS) delivered by the coil, define a starting pose of the coil, define a search strategy, including selection of a modality of TMS-induced biological feedback, definition of a number of stages of a search space, definition of an analysis algorithm for each stage, and definition of endpoint criteria for each stage, the search space comprising an array of locations, orientations and intensities to be stimulated, define the search space around the starting pose to be stimulated by the TMS delivery while obtaining the TMS-induced biological feedback during the TMS delivery based at least in part on the analysis algorithm, enable delivery of the TMS via the coil and obtain the TMS-induced biological feedback during the TMS delivery, analyze the TMS-induced biological feedback, test endpoint criteria for optimal aiming of the TMS delivery, the endpoint criteria to define a successful conclusion of a stage of the number of stages of the search space, enable delivery of the TMS for treatment of the subject when the endpoint criteria are met, deliver the TMS at a treatment site according to a defined stimulation site, and store the defined stimulation site in a storage for a future treatment session for the subject; and a storage coupled to the computer to store the defined stimulation site.

* * * * *

UNITED STATES PATENT AND TRADEMARK OFFICE
CERTIFICATE OF CORRECTION

PATENT NO. : 9,265,965 B2
APPLICATION NO. : 13/628509
DATED : February 23, 2016
INVENTOR(S) : Peter T. Fox and Jack L. Lancaster

Page 1 of 1

It is certified that error appears in the above-identified patent and that said Letters Patent is hereby corrected as shown below:

In the Claims

Column 10, Claim 5:
Line 46, "TMS-induced, movement TMS-induced alteration" should be --TMS-induced movement, TMS-induced alteration--.

Signed and Sealed this
Fourteenth Day of June, 2016

Michelle K. Lee
*Director of the United States Patent and Trademark Office*